(12) United States Patent
Becker et al.

(10) Patent No.: US 8,502,866 B2
(45) Date of Patent: Aug. 6, 2013

(54) VIDEO RECORDING DEVICE FOR A WELDER'S HELMET

(75) Inventors: William Joshua Becker, Manitowoc, WI (US); Eric Sommers, Appleton, WI (US); Kenneth S. Dobson, Northville, MI (US)

(73) Assignee: Illinois Tool Works Inc., Glenview, IL (US)

( * ) Notice: Subject to any disclaimer, the term of this patent is extended or adjusted under 35 U.S.C. 154(b) by 730 days.

(21) Appl. No.: 12/402,430

(22) Filed: Mar. 11, 2009

(65) Prior Publication Data

US 2009/0231423 A1 Sep. 17, 2009

Related U.S. Application Data

(60) Provisional application No. 61/036,750, filed on Mar. 14, 2008.

(51) Int. Cl.
*H04N 5/253* (2006.01)

(52) U.S. Cl.
USPC ............... 348/82; 348/61; 348/376; 345/8; 345/9

(58) Field of Classification Search
USPC .................. 348/82, 61, 376; 345/8
See application file for complete search history.

(56) References Cited

U.S. PATENT DOCUMENTS

| 5,644,324 | A  | * | 7/1997 | Maguire, Jr. ............... 345/9 |
| 6,078,021 | A  | * | 6/2000 | Chang ................. 219/121.63 |
| 6,456,261 | B1 | * | 9/2002 | Zhang ........................ 345/8 |
| 6,734,393 | B1 | * | 5/2004 | Friedl et al. ............. 219/132 |
| 7,271,894 | B2 | * | 9/2007 | Devitt et al. ........... 356/241.1 |
| 7,534,005 | B1 | * | 5/2009 | Buckman ................. 362/105 |
| 8,009,229 | B1 | * | 8/2011 | Peterson .................. 348/376 |
| 2003/0001950 | A1 | * | 1/2003 | Eriksson .................... 348/61 |
| 2005/0005308 | A1 | * | 1/2005 | Logan et al. ............ 725/135 |
| 2011/0186615 | A1 | * | 8/2011 | Gatlin et al. ............ 228/102 |

FOREIGN PATENT DOCUMENTS

| WO | 0158399 A1 | 8/2001 |
| WO | 2005102230 A1 | 11/2005 |

* cited by examiner

*Primary Examiner* — Tammy Nguyen
(74) *Attorney, Agent, or Firm* — Fletcher Yoder P.C.

(57) ABSTRACT

A weld recording system mounted in or on a welding helmet is provided. The weld recording system includes a camera assembly unit, a power supply unit, a processor, and removable memory. The weld recording system interfaces with lens control circuitry, an optical sensor, a welding power supply, and a helmet position sensor. Logic is provided for the triggering and recording of video and audio signals, which are eventually stored in a file for future reference. Transmission of signals from one or more welders to a monitoring station for eventual display is presented. An image processing algorithm is provided to combine multiple images with varied exposure times into a visual image of the weld and its surroundings.

29 Claims, 5 Drawing Sheets

VIDEO RECORDING DEVICE FOR A WELDER'S HELMET

CROSS REFERENCE TO RELATED APPLICATIONS

This application is a Non-provisional Patent Application of U.S. Provisional Patent Application No. 61/036,750, entitled "Video Recording Device for a Welder's Helmet", filed Mar. 14, 2008, which is herein incorporated by reference.

BACKGROUND

The invention relates generally to welding systems, and more particularly, to methods and systems for recording welding operations for later review, analysis, teaching, and so forth.

Welding is a process that has increasingly become ubiquitous in all industries. While such processes may be automated in certain contexts, a large number of applications continue to exist for manual welding operations performed by skilled welding technicians. However, as the average age of the skilled welder rises, the future pool of qualified welders is diminishing. Furthermore, many inefficiencies plague the welding training process, potentially resulting in injecting a number of improperly trained students into the workforce, while discouraging other possible young welders from continuing their education. For instance, class demonstrations do not allow all students clear views of the welding process. Additionally, instructor feedback during student welds is often prohibited by environmental constraints.

Inefficient weld training gives rise to several engineering problems. For example, such training typically requires the use of costly practice materials (e.g., weld coupons, welding wire, welding gas, etc.), the wasting of which should be avoided. Moreover, laboratory and instructor time spent on training and on perfecting technique makes maximizing the speed and quality of training of welding students key. Current weld training assistance systems fall short of providing a satisfactory solution to these challenges because they are plagued with technical difficulties and prohibitive operating costs. Therefore, there exists a need for improved techniques that can offer better review and analysis of welding operations. Such techniques could be used in production environments, as well as for training, allowing instructors to both critique student welds and visually demonstrate correct technique.

BRIEF DESCRIPTION

The present invention provides a novel technique for capturing and reviewing welding operations designed to respond to such needs. The technique allows for capturing video and audio data during a welding operation, along with, where desired, actual welding parameters measured or calculated at times corresponding to the video and audio data. In particular, the invention provides a weld recording system mounted in or on a welding helmet that includes a camera assembly unit, a power supply unit, a processor, and removable memory. The weld recording system may interface with lens control circuitry, an optical sensor, a welding power supply, and/or a helmet position sensor. Logic may be provided for the triggering and recording of video and audio signals, which are eventually stored in a file for future reference. Signals may be transmitted from one or more welders to a monitoring station for eventual display. An image processing algorithm is provided to combine multiple images with varied exposure times into a visual image of the weld and its surroundings. Live or near-live playback may be provided, such as for instruction, monitoring, and so forth.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
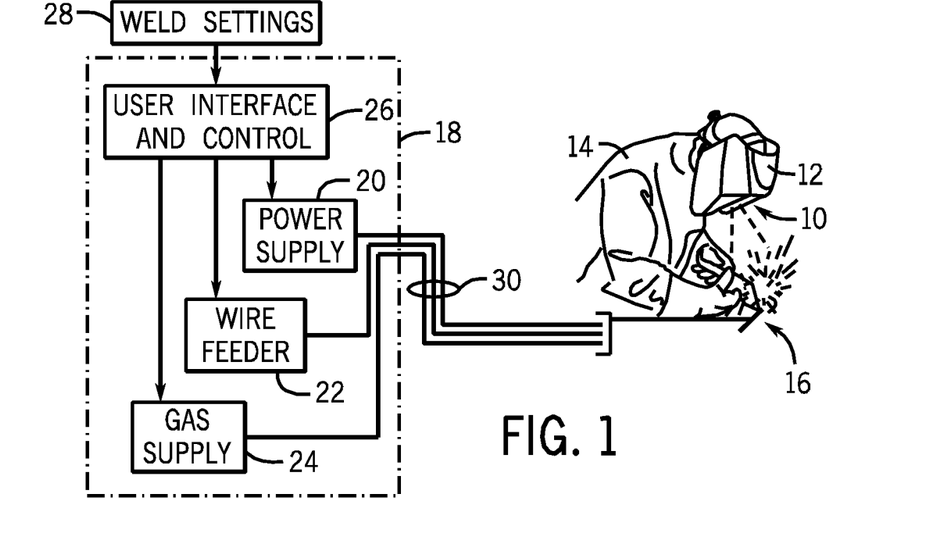
FIG. 1 is a diagrammatical illustration of a welder wearing a helmet adapted for recording a welding operation in accordance with aspects of the present invention.

FIG. 1 illustrates a weld recording system 10 positioned in or on a welding helmet 12 worn by a welder 14. The field of view of the weld recording system 10 is designed to encompass at least the area where the welding operation 16 is occurring, including both the welding arc and at least a portion of the surrounding environment. In certain embodiments, this field of view may overlap partially or entirely with the field of view of the welder 14. The welding operation will typically be powered and controlled by a welding system 18, which interfaces with a welding torch manipulated by the welder. In the illustrated embodiment, welding system 18 is comprised of a power supply 20, a wire feeder 22, and a gas supply 24 that provide power, welding wire, and gas, respectively, for the welding operation 16. The power supply 20 may be but is not limited to inverter circuitry that produces DC or AC output and that may operate in constant current or constant voltage regimes, or both. The wire feeder 22 provides a controllable feed of welding wire, such as for metal inert gas (MIG) operations. The gas supply provides shielding gas for such operations.

A user interface 26 allows the welder 14 to control the welding parameters, such as current, voltage, wire feed speed, specific programmed welding regimes, and so forth. Since the weld recording system 10 may be shared by multiple users, customized weld settings 28 may be stored and input into the welding system 18. These settings may include but are not limited to pre-weld and post-weld buffer times, number of welds to record, which parameters to display during the weld, and so forth. It should be noted that such recording parameters and similar options may be set on a user interface of the recording system within the welder's helmet, or by storing such parameters on memory circuitry associated with the recording system described below. The welding system 18 provides power to a welding torch, as well as wire and gas through a weld cable 30. It should be noted, however, that the present welding operation recording techniques are not limited to this or any particular welding system design, and may be used with tungsten inert gas (TIG), stick, or any other suitable welding systems.

Figure 2:
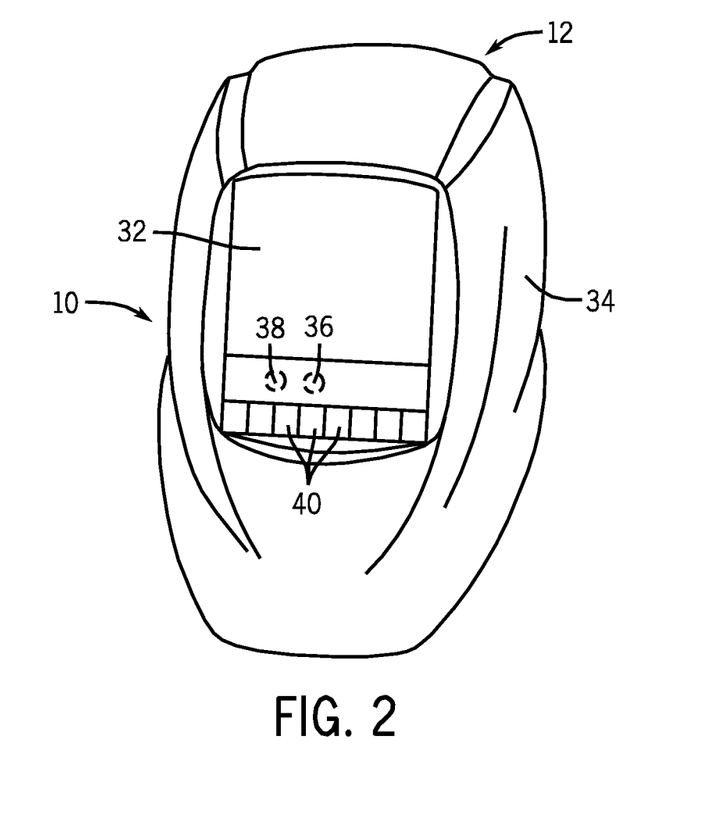
FIG. 2 is a front view of an exemplary welding helmet for use in the system of FIG. 1, illustrating the components that may be integrated with the welding helmet.

FIG. 2 illustrates the welding operation recording system 10 embedded in the welding helmet 12. The welder 14 views the welding operation 16 through a dark or autodarkening lens 32, which is mounted to the shell 34 of the welding helmet 12. In one embodiment, a camera assembly 36 for capturing video signals and a microphone 38 for capturing audio signals are mounted below the lens 32. In other embodiments, one or both of these components may be mounted in other locations in or on the welding helmet 12. Photovoltaic cells 40 may also be mounted in or adjacent to the lens 32 for capturing light energy from either ambient light during non-welding periods or the welding arc during welding. These photovoltaic cells 40 may be used to supply some or all of the electrical power required by the recording system, and may be placed in any location on the welding helmet.

Figure 3:
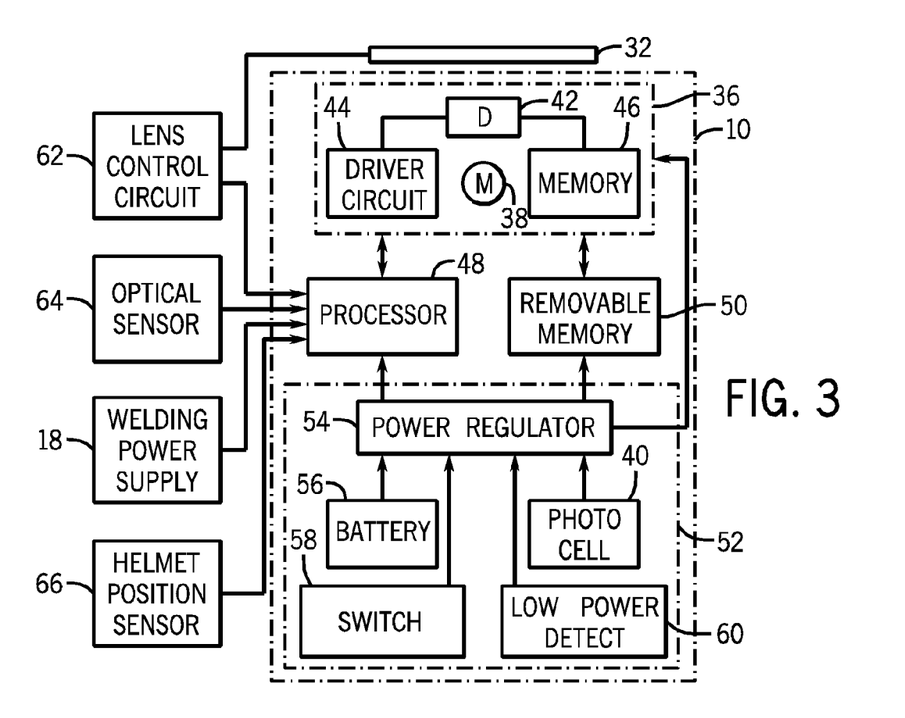
FIG. 3 is a block diagram of an exemplary welding operation recording components and inputs it may receive during welding operation.

FIG. 3 is a block diagram illustrating an exemplary embodiment of the welding recording circuitry and inputs it may receive during a welding operation. The first component of the weld recording system 10 is the camera assembly 36. This module may include a microphone 38, a digital detector 42 (e.g., a CCD or CMOS circuit), a driver circuit 44, and memory 46. The microphone 38 may be used to record audio signals during the welding operation or to receive user commands for system processing. The detector 42, which may be a charge coupled device or any other suitable detector captures video images and converts them to electrical signals for recoding. Driver circuit 44 is provided for providing drive signals for operation of the camera. Camera memory 46 may be the primary means of storing certain information, particularly camera settings, recording settings, and so forth. The camera assembly may be a pre-packaged unit that is added to the helmet and interfaced with the other recording components described below.

The camera assembly 36 interfaces with both the processor 48 and removable memory 50. It should be noted that the processor 48 will typically either include its own memory, or may be associated with memory, such as for storing algorithms and instructions executed by the processor during operation, as well as image data on which the processing is performed. The processor 48 may communicate with the camera assembly 36 to set camera parameters such as exposure time and gain (e.g., sensitivity). Furthermore, it may perform image processing algorithms and may compress the video into a standard format. In certain embodiments, the processor 48 may store the video on the removable memory 50, which may be a USB flash drive, SD card, etc. The processor 48 may also receive and process information originating from components external to the weld recording system 10.

A power supply 52 module provides power for the system, and may include a central power regulator 54 that receives power from a battery 56 and/or photovoltaic cells 40, a switch 58, and a low power detector 60. The power regulator 54 may consist of one or more DC-DC voltage regulators that convert battery power and/or light energy into power levels that the weld recording system 10 can use and supplies the camera assembly 36 with power. The battery 56 may be but is not limited to lithium-ion, lithium-polymer, AA, or coin style batteries that may be rechargeable or non-rechargeable. The switch 58 allows the user to manually power the system off or on. In certain embodiments, a passive switch, such as a toggle switch or push button, may be used. In other embodiments, an active switch, such as a touch or voice sensor, may be chosen instead or in addition to the manual switch. The low power detector 60 indicates when the device needs to be recharged or the batteries need to be replaced. In certain embodiments, it may consist of a low-battery monitor or a comparator used with a constant voltage reference. In some embodiments, an indicator, such as an LED, may alert the user through flashing or other means that the battery needs to be recharged or replaced.

The processor 48 may interface with external components, such as to receive signals for operation of the system or for recording of signals. For example, in the illustrated embodiment, the processor may receive signals from lens control circuitry 62, an optical sensor 64, a welding power supply 18, and a helmet position sensor 66. Where an auto-darkening lens is present, lens control circuitry 62 may provide a signal indicative of darkening of the lens (i.e., that a welding operation has begun), and this signal may be transmitted to the processor 48. In certain embodiments, an optical sensor 64 may detect the onset of a welding operation and trigger video recording via communication with the processor 48. The helmet position sensor 66 may detect whether the helmet is raised (i.e., no welding operation will begin) or lowered (i.e., a welding operation may be initiated at any time) and transmits a signal to the processor 48, which may be used as a basis for determining when video recording should be initiated.

It should be noted that, while reference is made in the present discussion to video and/or audio recording, the present techniques also contemplate live, real time or near real time monitoring of welding operations by use of the helmet camera and other systems described. For example, as described below, the recording of welding operations may include storing of signals or data representative of video and/or audio for later access, viewing, and so forth. Even during welding operations, however, similar viewing can be done by transmitting signals from the video/audio capture system to one or more monitors that may be local to or remote from the location where the welding operation is ongoing.

Figure 4:
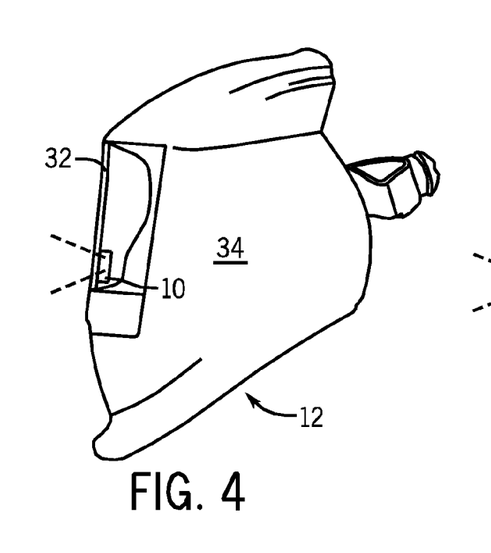
FIG. 4 is a side view of the welding helmet shown in FIG. 3 illustrating placement of the recording system behind the lens.

FIG. 4 is a side view of a welding helmet 12 illustrating placement of the weld recording system 10 behind the lens 32 in the shell 34 of the welding helmet 12. This configuration allows for the field of view of the weld recording system 10 to include video of the weld as the welder would view it, and shields the camera behind the lens 32. In this embodiment, all light reaching the camera sensor 42 would have passed through the lens 32. In certain embodiments, the processor 48 may execute an image processing algorithm, which uses the relationship between exposure time and signal strength (e.g., pixel brightness) to calculate the light intensity presented to the welder 14, indicating whether the lens shade is properly set. It should be noted that the processor may use such image data and analysis to determine whether welding has started or stopped, and to begin or terminate video and/or audio capture (or to start or stop buffer overwriting, as described below). Moreover, certain algorithms implemented by the processor could alter the image data, such as to remove greenish tint that may result from placement of the camera detector behind the helmet lens. Similarly, the processor may implement an image stabilization algorithm to smooth movement apparent in playback of the images in a stream. The processor may also implement one or more video and/or audio compression algorithms on the image and/or audio data.

Figure 5:
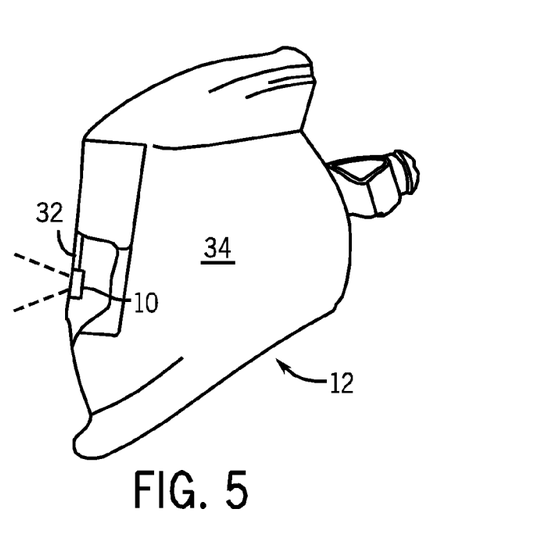
FIG. 5 is a side view of the welding helmet shown in FIG. 3 illustrating placement of the recording system below the lens.

FIG. 5 is a side view of a welding helmet 12 illustrating placement of the weld recording system 10 below the lens 32 in the shell 34 of the welding helmet 12. In this embodiment, the field of view of the weld recording system 10 would be in direct view of the work area and welding arc. In such an embodiment, a weld recording system 10 that allows for very short exposure times and quick reaction times to the change from ambient to weld lighting may be advantageous. Such a system may utilize an optical sensor with very short exposure time to capture the bright welding arc without saturating the images. Since the weld recording system 10 may not be placed behind the lens 32 in this embodiment, the tint from the lens 32 will be avoided, and the video may include color images.

Figure 6:
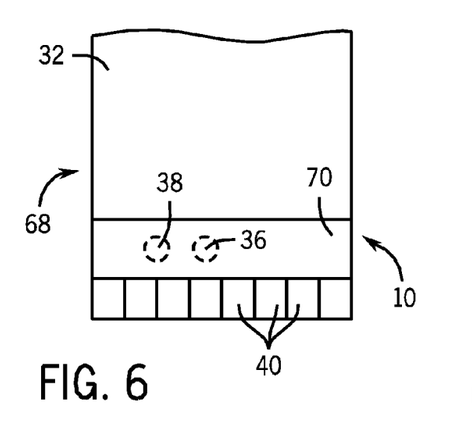
FIG. 6 is a front elevation view of an exemplary lens assembly for a welding operation recording system.

FIG. 6 is a front view of one embodiment of the lens assembly 68, which houses multiple components that fit into the front of the welding helmet 12. In this embodiment, the lens 32 sits adjacent to the weld recording system 10, which is comprised of the camera assembly 36, microphone 38, and associated circuitry 70. Since the weld recording system 10 is in direct view of the weld in this configuration, photovoltaic cells 40 may be used to harvest some of the light energy from the weld to power the electronics of the system 10.

Figure 7:
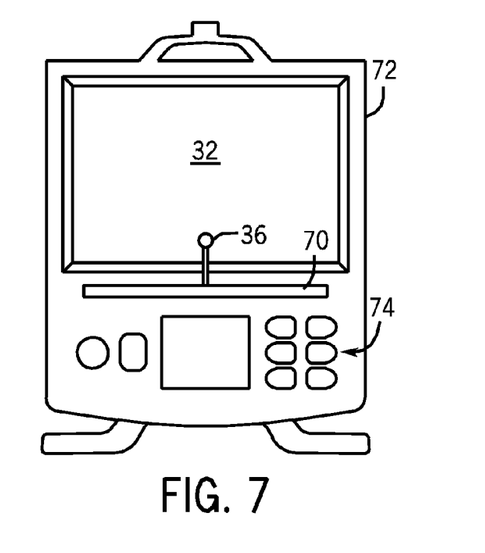
FIG. 7 is a front view of an exemplary lens cartridge and holder illustrating a possible placement of system components.

FIG. 7 illustrates one possible placement of the camera assembly 36 behind the lens 32 mounted on the lens cartridge and holder 72. In this embodiment, the camera assembly 36 extends from the circuitry 70 below the lens 32 to a position behind the bottom portion of the lens 32. The helmet interface 74, which allows the user to control the operation of the welding helmet 12, sits below the camera assembly circuitry 70. The lens cartridge and holder 72 may then be attached to the welding helmet 12 via the appendices on the top and bottom of the holder 72. It should be noted that the camera assembly (or any part of the recording system) may be integrated into an auto-darkening lens cartridge or any support structures provided for the lens and its associated circuitry. It should also be noted that the camera, or at least the digital detector of the camera, may be shielded from ambient light within the helmet structure, or within the lens structure, or by a separate shield, to prevent or limit the exposure of the detector to stray light that does not pass through the lens.

In one embodiment of the present invention, the processor 48 may execute various exposure-adjusting algorithms that vary exposure time from frame to frame. With very short exposure times, a frame may be acquired in which the welding arc would be visible while the surrounding area would appear dark. With longer exposure times, a second frame may be acquired in which the welding arc would appear as a bright spot while the surrounding environment would be visible. The exposure-adjusting algorithm may combine these different frames to create a hybrid image that allows for visualization of both the welding arc and the surrounding environment. For implementation, the short exposure time is set so that the brightest points of the image are just below the saturation point of the digital detector. Similarly, the long exposure time is set so that the brightest points in the surrounding area are just below the saturation point of the detector.

Figure 8:
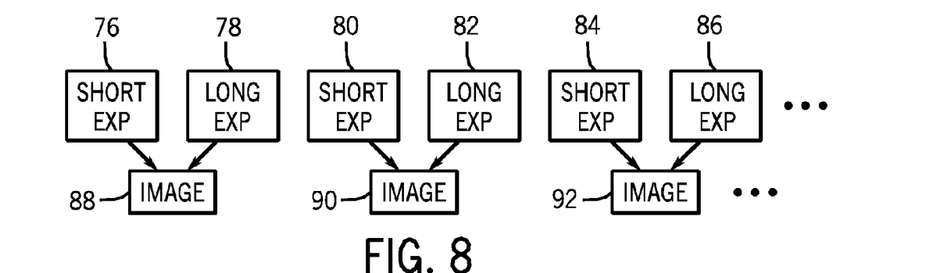
FIG. 8 is a block diagram illustrating exemplary image processing logic that may be used to create visible images of welding operations.

Exemplary logic behind one embodiment of the aforementioned algorithm is illustrated in FIG. 8. In this approach, a succession of alternating short then long exposure time frames 76-86 is first acquired. Subsequently, each pair of frames, one with a short exposure time and one with a long exposure time, are combined to create a visible image of both the welding arc and its surroundings. Each frame contributes to only one visible image, and the final video rate corresponds to half of the frame rate of the camera. For instance, the first short exposure frame 76 and the first long exposure frame 78 are combined to create the first visible hybrid image 88. The short exposure frame 76 captures the welding arc while the long exposure frame 78 captures the surrounding environment. Similarly, the second short exposure frame 80 and the second long exposure frame 82 are combined to create the second visible hybrid image 90. Finally, the third short exposure frame 84 and the third long exposure frame 86 are combined to create the third visible hybrid image 92 shown. The processor 48 would proceed combining the short and long frames throughout the image acquisition period.

Figure 9:
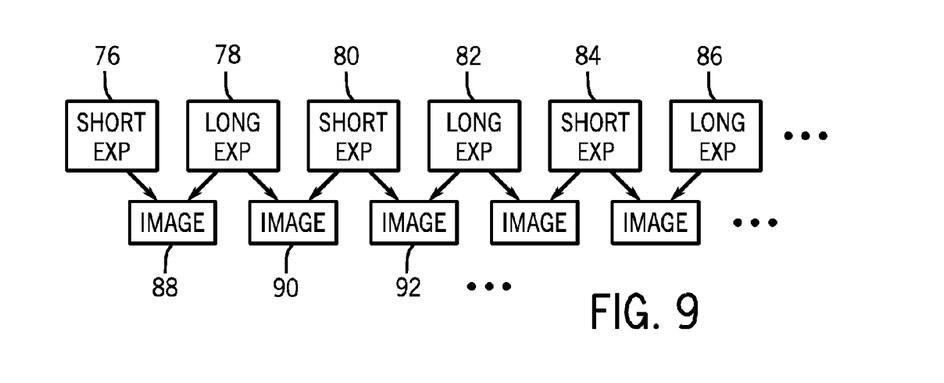
FIG. 9 is a block diagram illustrating image other exemplary processing logic that may be used to create visible images of welding operations.

Exemplary logic behind another approach to exposure-adjusting is illustrated in FIG. 9. Here, a succession of alternating short then long exposure time frames 76-86 is first acquired. Pairs of one short and one long exposure frame are then combined to create a visible image of both the welding arc and its surroundings. In this embodiment, each frame contributes to two visible images, and the final video rate is equal to the frame rate of the camera. For instance, the first short exposure frame 76 and the first long exposure frame 78 are combined to create the first visible hybrid image 88. Subsequently, the first long exposure frame 78 is combined with the second short exposure frame 80 to create the second visible hybrid image 90. The second short exposure frame 80 is then combined with the second long exposure frame 82 to form the third visible hybrid image 92. The processor 48 would proceed similarly combining the short and long frames throughout the image acquisition period. The present invention covers all combinations of frames with varied exposure times used to generate a visual image of the welding operation and its surroundings.

Figure 10:
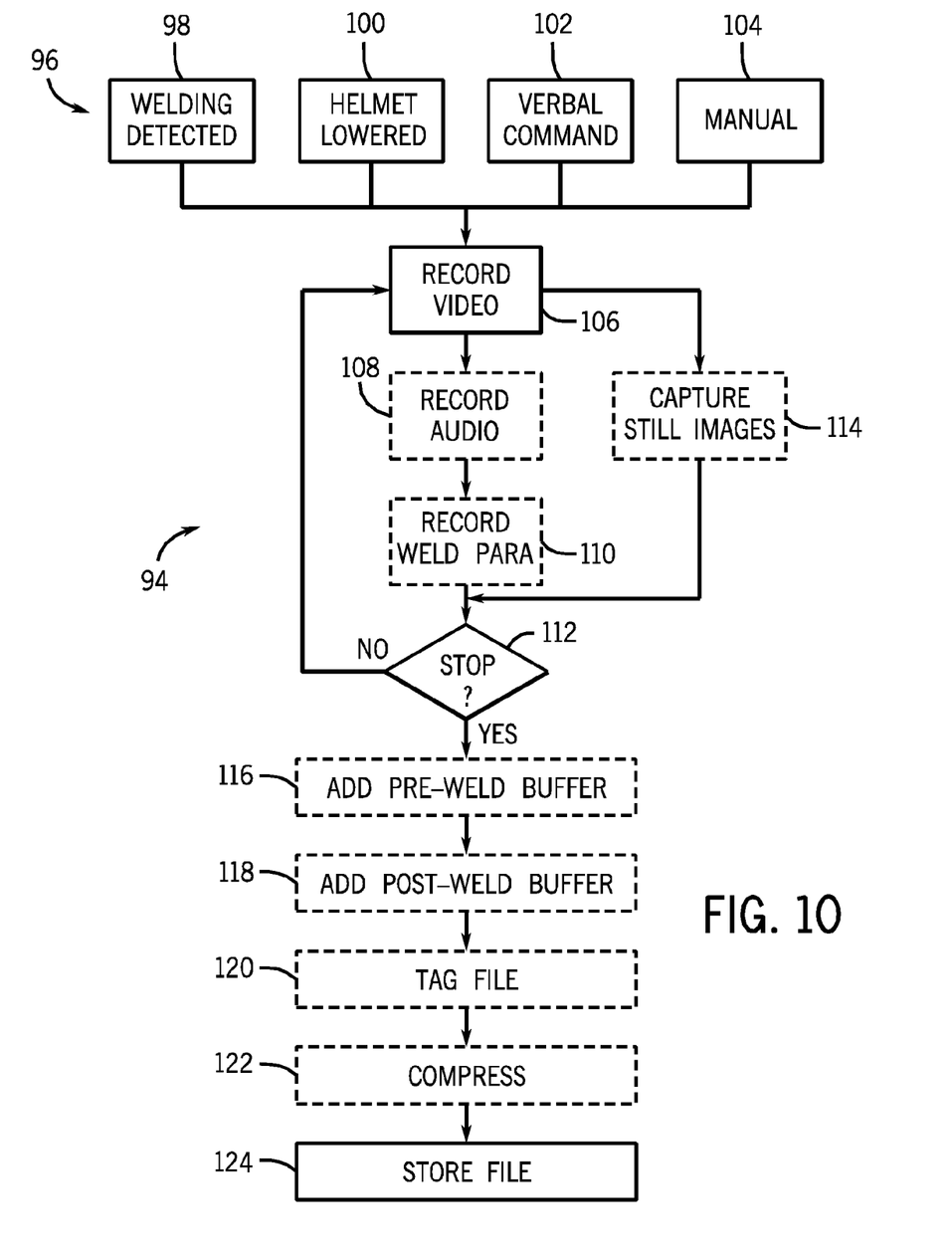
FIG. 10 is a block diagram illustrating exemplary logic for recording a welding operation.

FIG. 10 is a block diagram illustrating exemplary logic 94 behind certain aspects of the operation of the weld recording system 10. Weld recording begins when one or more of the initiating events 96 occur. These events may include detection of initiation of a welding operation, as indicated by reference numeral 98, detection of lowering of the welding helmet, as indicated by numeral 100, receipt of a verbal command, as indicated by numeral 102, and manual triggering (e.g., switching), as indicated by numeral 104. For example, onset of a welding operation may be detected optically either by sensing the darkening of the lens 32 or the brightness of the work area. It should be noted that such optical detection may be done by the camera detector or by a separate optical sensor. Moreover, the onset of the welding operation may be detected by analysis performed by the processor discussed above, such as to recognize a level of brightness corresponding to welding, sharp transitions in brightness, and so forth. Video recording 106 can also be triggered when the welder 14 lowers the welding helmet 12 to a working position in preparation for a weld. Alternatively, recording may begin when the welding helmet is lowered, as detected by a position sensor, indicating that a welding operation may begin at any time. The welder 14 may also verbally or manually trigger video recording regardless of helmet position. For instance, the welder may want to capture the setup process before the weld actually begins and may therefore want to initiate recording while the helmet is still in a nonworking position. It should be noted that any particular implementation may include one or more of these triggering mechanisms, or indeed others as well.

In certain embodiments, the user may want to record audio 108, record weld parameters 110, and/or capture still images 114. For example, the user may want to record audio comments during the weld for future reference. Additionally, because in many types of welding a proper weld sounds different from an improper weld, the audio recording may aid in future evaluations of the welding operation. Moreover, the welder may wish to record audio signals so as to point out how the operations are proceeding, instruct viewers on proper techniques, and so forth. In certain embodiments, the weld parameters the user may choose to record may include but are not limited to voltage, amperage, wire feed speed, stick out, travel speed, and torch angles. These parameters may be displayed in real time to observers, or may be played back later via a user interface. Such parameters may be instructive insomuch as they affect the actual weld and the sights and sounds that may be recorded of the welding operation.

The weld recording system 10 may cycle through a logical stop block 112 where video recording can either cease or continue. A stop can be triggered, for example, by a detection of a weld ending point, raising the helmet, a verbal command, or a manual switching. In general, stopping of recording may be triggered by similar events, although typically in an opposite sense, as caused the recording to begin (e.g, detection of dimming of sensed light, sharp transitions from a bright condition to a less bright condition, and so forth). In certain embodiments, the user may choose to add a pre-weld time buffer 116 and/or a post-weld time buffer 118 around the duration of the welding operation of interest during which the device will record even though a weld is not taking place. Such additional recording may provide a good lead-in and tail-off of the recording. In certain embodiments, the user may wish to tag certain video or audio files, as indicated by block 120, for easy future identification either before or after they are captured. Such tags may be created, for example, by depressing a button, and an indication of the tag may be apparent (e.g., by a graphical indication, such as a flag, asterisk, or any other label) in or with a file name which may appear on a listing of files of recorded welding operations accessed from the system memory. These tags may also include audio messages, audio signals, or video signals such as user name or number, at a point in the operation that may be of particular interest. Such tags may be inserted before, after or during welding operations recorded by the system. Moreover, the user may also want to compress the resulting video or multimedia file, as indicated by block 122, to a standard form for later use. Where desired, the system may be designed to perform such compression by default. Such compression may be performed in real time or near real time, as the data is being recorded. Finally, the file is stored 124 in memory.

Here again, while the logic summarized in FIG. 10 calls for storing of data representative of the welding operation (which may include video, audio, and/or welding data), such as for later viewing, the system may be utilized for real time or near real time monitoring of such welding operations. That is, signals may be sent from the system to one or more monitors during the welding operation such that viewers may see the progression of the welding operation as it is carried out. This may be done with or without actual storage of the data for later viewing.

It should also be noted that the buffering of pre-weld recorded data and post-weld recorded data may be handled in various ways. For example, in practice, the system may be set to continuously record video and/or audio signals when not in a standby or off state. That is, the system may enter into an active state upon the welder lowering the helmet. Once in an active state, the system may record video data and maintain a buffer of such data, periodically overwriting recorded data until an actual welding operation begins or until the operator signals actual recording to begin. Once such initiating signals are received, then, the overwriting of the buffer may stop, and the most recently recorded data from the buffer may serve as the beginning portion of a file or file section. Similarly, once recording stops, the last portion of the recorded data may be saved as a conclusion to the recorded welding operation. In the case of "looped" buffer overwriting, then, the system may again begin to overwrite the buffer until another recording begins by any of the triggering events summarized above.

Figure 11:
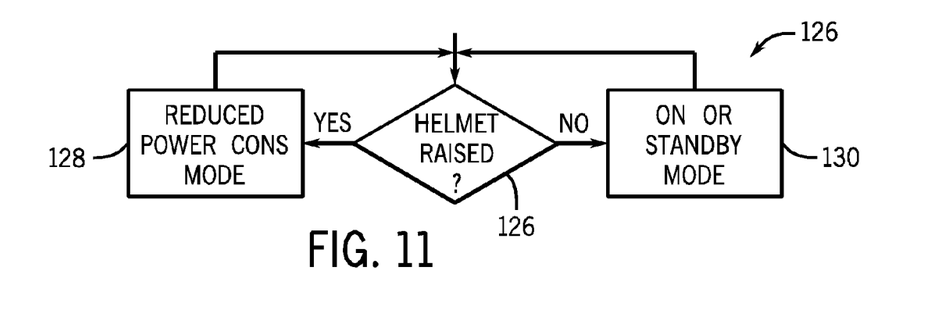
FIG. 11 is a block diagram illustrating additional exemplary logic for recording a welding operation.

FIG. 11 is a block diagram illustrating exemplary logic 126 for an energy saving routine that may be built into the present invention. For example, when the welding helmet 12 is raised, an assumption can be made that a welding operation is not occurring, and the device may cycle into a reduced power consumption mode 128 to save energy. When the welding helmet 12 is not raised (i.e., is lowered), the device cycles into either on or standby mode 130 to allow for recording of the welding operation. This logic allows energy to be saved during periods of inactivity.

Figures 12, 13:
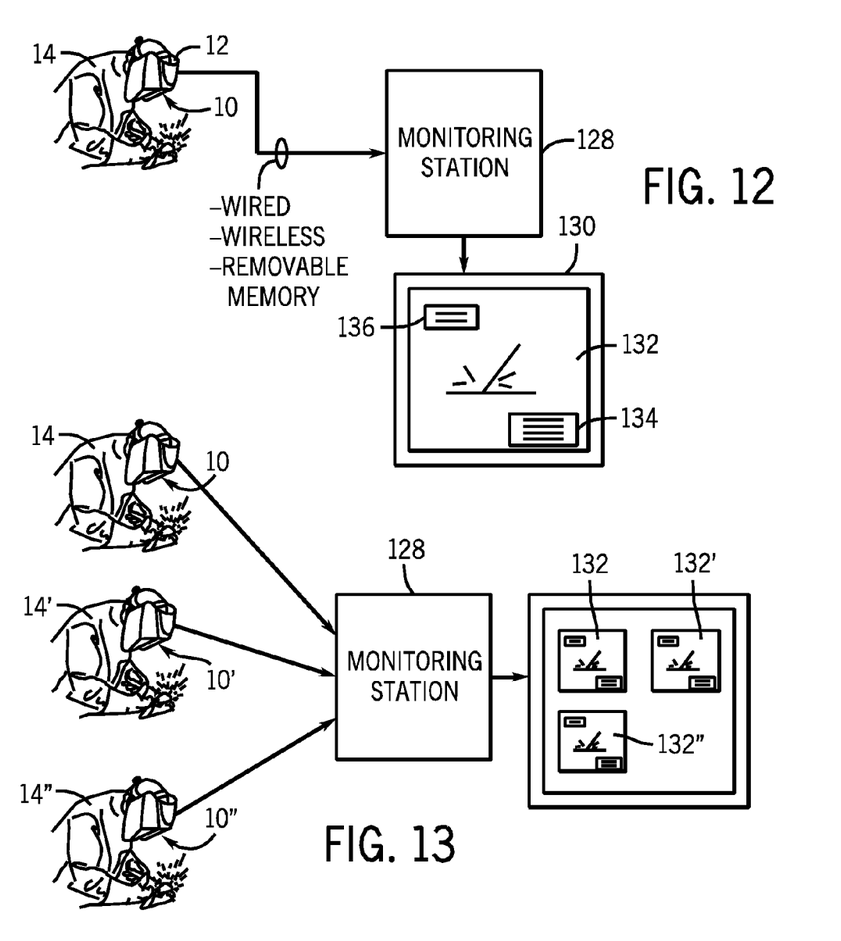
FIG. 12 is a diagrammatical representation of recording of a welding operation by transmitting signals to a monitoring station for display.
FIG. 13 is a diagrammatical representation of recording of multiple welding operations by transmitting signals to a monitoring station for display.

FIG. 12 is a diagrammatical view of an exemplary application of the overall system for real time monitoring or later viewing and analysis of a recorded welding operation. As noted above, in the welding operation a welder 14 will wear a welding helmet 12 equipped for recording. The recording system in the helmet may transmit signals to a monitoring station 128 for display or processing. In certain embodiments, the transmission of information will proceed via a wired or wireless connection. In other embodiments, removable memory taken from the camera assembly 36 may be the means of transfer. Moreover, as noted above, the system may allow for simultaneous monitoring and/or recording of weld parameters that can be associated with video and audio signals for display and analysis of the recorded welding operation. From the monitoring station 128, information may be transmitted to a display 130, which allows visualization of video recordings 132, weld data 134, and/or welder information 136 such as user identification name or number. The system may also be adapted to allow for monitoring and recording of multiple welding operations, as shown in FIG. 13. Such monitoring may be useful for analyzing performance of teams of welders, classes of welding students, and so forth. In this embodiment, multiple welders 14, 14', and 14" wearing welding helmets outfitted with weld recording systems 10, 10', and 10", respectively, transmit signals to the monitoring station 128. The monitoring station 128 then allows for viewing of the welding operations, as indicated by reference numerals 132, 132', and 132". Each welding operation may be recorded with video data, audio data and weld data, as in the case of a single welding operation.

As noted above, the usage of the systems outlined in FIGS. 12 and 13 may include real time or near real time observation of the welding operation by transmitting signals representative of captured video, audio and/or welding parameters to one or more monitors local to or remote from the location where the welding operation is being carried out. For instructional settings, for example, multiple monitors may receive feeds of such signals and display video (and play audio, and display welding parameters where desired and available) for students, welders, trainees, customers, and so forth.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for video capture of a welding operation comprising:
   a welding helmet;
   a lens disposed in the welding helmet through which a welder views the welding operation, wherein the lens is configured to filter light from the welding operation to produce filtered light suitable for viewing by the welder; and
   a video camera disposed in the helmet behind the lens for imaging a welding operation, wherein the video camera is configured to receive the filtered light.

2. The system of claim 1, comprising a microphone for capturing sound during the welding operation.

3. The system of claim 1, wherein the video camera is optically shielded from stray light that does not pass through the lens.

4. The system of claim 1, wherein the video camera is configured to automatically start or stop the video capture.

5. The system of claim 1, wherein the helmet comprises means for transmitting video signals, and wherein the system includes a monitor configured to receive the video signals and to display a presentation of the welding operation during the welding operation.

6. A system for video capture of a welding operation comprising:
   a welding helmet including a lens through which a welder views the welding operation, wherein the lens is configured to filter light from the welding operation to produce filtered light suitable for viewing by the welder;
   a video camera disposed in the helmet behind the lens for imaging a welding operation, wherein the video camera is configured to receive the filtered light; and
   a storage device for storing a data file including video data representative of the welding operation and from which the data file can be retrieved after termination of the welding operation.

7. The system of claim 6, further comprising a microphone disposed in or on the helmet for recording sounds during the welding operation, and wherein the storage device also stores audio signals representative of the sounds.

8. The system of claim 6, comprising means for detecting at least one welding parameter during the welding operation in cooperation with the video capture to permit simultaneous viewing of the welding operation via playback of the video capture and the welding parameters.

9. The system of claim 8, comprising wherein the data file includes indicia representative of the welding parameters superimposed into the video recording.

10. The system of claim 6, comprising means for automatically starting and stopping video capture of a welding operation.

11. The system of claim 6, wherein the helmet comprises means for transmitting video signals, and wherein the system includes a monitor configured to receive the video signals and to display a representation of the welding operation during the welding operation.

12. The system of claim 6, wherein the storage device stores multiple data files representative of different welding operations.

13. The system of claim 6, wherein the video camera is configured to record still images of the welding operation during video recording.

14. The system of claim 6, comprising a processor configured to process multiple separate images of the welding operation to create a video file.

15. A method for video capture of a welding operation comprising:
   automatically starting or stopping video capture of a welding operation via a video capture system including a camera mounted in a welding helmet behind a lens configured to filter light from the welding operation to produce filtered light suitable for viewing by a welding operator, wherein the camera is configured to receive the filtered light; and
   storing video signals representative of the welding operation.

16. The method of claim 15, comprising storing video signals representative of a successive welding operation without overwriting video signals representative of a previous welding operation.

17. The method of claim 15, wherein the video capture is started or stopped by movement of the welding helmet to a welding position or a non-welding position.

18. The method of claim 15, wherein the video capture system is placed in a reduced power consumption mode when the welding helmet is moved to the non-welding position.

19. The method of claim 15, wherein the video capture is started or stopped by operator commands.

20. The method of claim 15, wherein the video capture is started or stopped by detection of the presence or absence of an optical signal representative of whether the welding operation is proceeding or not.

21. The method of claim 20, wherein the optical signal is provided by a detector of the video capture system.

22. The method of claim 20, wherein the optical signal is provided by a detector separate from the video capture system.

23. The method of claim 15, wherein storing the video signals includes storing video signals for a duration before the welding operation is initiated.

24. The method of claim 23, wherein the video capture system continuously detects, stores, and overwrites data representative of video signals until a welding operation is detected.

25. The method of claim 15, wherein storing the video signals includes storing video signals for a duration after the welding operation is terminated.

26. The method of claim 15, comprising recording audio signals during the welding operation and storing the audio signals.

27. The method of claim 26, wherein the audio signals are stored with the video signals in a multimedia data file.

28. The method of claim 15, comprising recording at least one welding parameter during the welding operation in cooperation with the video capture to permit simultaneous viewing of video playback of the welding operation and the welding parameters.

29. The method of claim 28, comprising superimposing indicia representative of the welding parameters into the video recording.

* * * * *